United States Patent
Negron

(10) Patent No.: US 6,964,653 B2
(45) Date of Patent: Nov. 15, 2005

(54) MULTI-USE HYGIENIC CLEANSING DEVICE

(76) Inventor: Felipe Negron, 170 Avenue C #12G, New York, NY (US) 10009

( * ) Notice: Subject to any disclaimer, the term of this patent is extended or adjusted under 35 U.S.C. 154(b) by 0 days.

(21) Appl. No.: 10/066,619

(22) Filed: Feb. 6, 2002

(65) Prior Publication Data

US 2003/0181886 A1 Sep. 25, 2003

(51) Int. Cl.[7] .................. A61M 5/24; A61M 31/00; A61M 5/00; A61M 5/178
(52) U.S. Cl. ................. 604/200; 604/279; 604/39; 604/187; 604/514
(58) Field of Search ................. 604/200–279, 604/39, 187, 514, 911, 2, 150, 85, 113, 184, 181, 60, 57, 171, 36; 222/538; 600/210, 220, 257

(56) References Cited

U.S. PATENT DOCUMENTS

| | | | |
|---|---|---|---|
| 3,581,743 A | 6/1971 | Stein et al. | |
| 4,405,321 A | 9/1983 | Budoff | |
| 4,650,470 A | * 3/1987 | Epstein | 604/149 |
| 4,704,102 A | * 11/1987 | Guthery | 604/28 |

* cited by examiner

Primary Examiner—Nicholas D. Lucchesi
Assistant Examiner—Roz Maiorino
(74) Attorney, Agent, or Firm—Muserlian, Lucas and Mercanti

(57) ABSTRACT

A reusable bacteria inhibiting hygienic device for vaginal/colon and external genital cleansing suited for use while seated on the toilet or standing in a tub respectively, including a rigid stationary/flexible portable container proficient in delivering a sufficient amount of douche, colon or external cleansing preparation provided with a vented cap, a volume sensitive valve, a retainer cap a short length of tubing with threads attached to retainer, and the other end of short length of tubing attached to the top of a control valve with backflush prevention ballcheck, an adequate length of tubing with one end attached to bottom of control valve and opposite end of adequate length of tubing attached to acessory of choice.

16 Claims, 6 Drawing Sheets

MULTI-USE HYGIENIC CLEANSING DEVICE

This invention relates to an improved douche, colon and genital cleansing device and especially as an improvement to a reusable douche, colon and genital cleansing preparation container, and its components which are capable of being used while seated on a toilet or standing in a tub.

BACKGROUND OF INVENTION

Many women find rinsing away remaining sangure fluid a beneficial aspect of douching shortly after the menstrual cycle. While approximately the majority of women in this country douche, all cleanse externally. Colon cleaning also provides a health benefit to the user. Colon cleansing is also a process that is beneficial to both female and their male counterparts. Presently, by today's standards, the available douches and enema preparations are enema preparations are regarded as safe, convenient, but are ineffective in volume for proper cleansing. Multiple containers are required to perform an effective cleansing.

In addition, disposable douches create more waste for the environment. They also have the propensity to allow air into the vagina which consequently can cause painful discomfort to the user. Another problem associated with disposable douches is the possibility of a backflush which will occur if the user releases prior art squeeze bottles without removing the transfer nozzle from vaginal or anal cavity. The result of this is the contamination of the preparation within the container. A study published by the American Journal of Public Health states that regular douching may reduce a woman's chance of becoming pregnant during a particular month by approximately thirty percent. Douching often changes the delicate chemical balance of the vagina and can make a woman more susceptible to vaginal irritations and infections.

Prior art of reusable douche/enema devices are constructed of rubber and the douche/enema preparation is administered directly from the rubber bag. These types of douche/enema bags are very dangerous. It has been found that these rubber douche/enema bags harbor a perfect environment for a variety of pathogens which increases their ineffectiveness, the introduction of air into the vaginal or anal cavity and potential danger due to pathogen growth within the bag. Also, prior art advocated the use of tap water which by today's standards is not acceptable for internal use.

THE OBJECT OF THIS INVENTION

It is the intent of the present invention to provide an improved, reusable douching, enema and genital cleansing delivery device, a cleansing that is safe, convenient and efficient while seated on a toilet or standing in the tub respectfully.

Another object is to avoid the problems associated with prior art douching and enema devices.

A further object of this invention is to provide a volume sensitive valve to dramatically reduce the introduction of air into the vagina or anal cavity and to prevent the backflush effect that will contaminate the preparation in the container when administering a douche or enema preparation which is accomplished via the use of a ball check incorporated within the control valve.

Another object of this invention is to facilitate the use of the hygienic feminine/colon and genital cleansing device by allowing the one hand manipulation of said device.

Furthermore, the use of Microban Technology will inhibit the growth of bacteria within the container and its components.

Varios other object and advantages of the invention will become obvious from the following detailed description.

SUMMARY OF INVENTION

In accordance with the invention, the douche/enema and genital cleansing device comprises a rigid/flexible container, a retainer secured to lower most portion of rigid/flexible container, a short length of flexible hollow tubing affixed to the lower portion of said retainer, a control valve connected to the lowermost portion of the flexible hollow tubing, an adequate length of flexible hollow tubing connected to lowermost portion of control valve and a nozzle of choice to the lowermost portion of adequate length of flexible tubing.

DESCRIPTION OF A PREFERRED EMBODIMENT

Figure 1A:
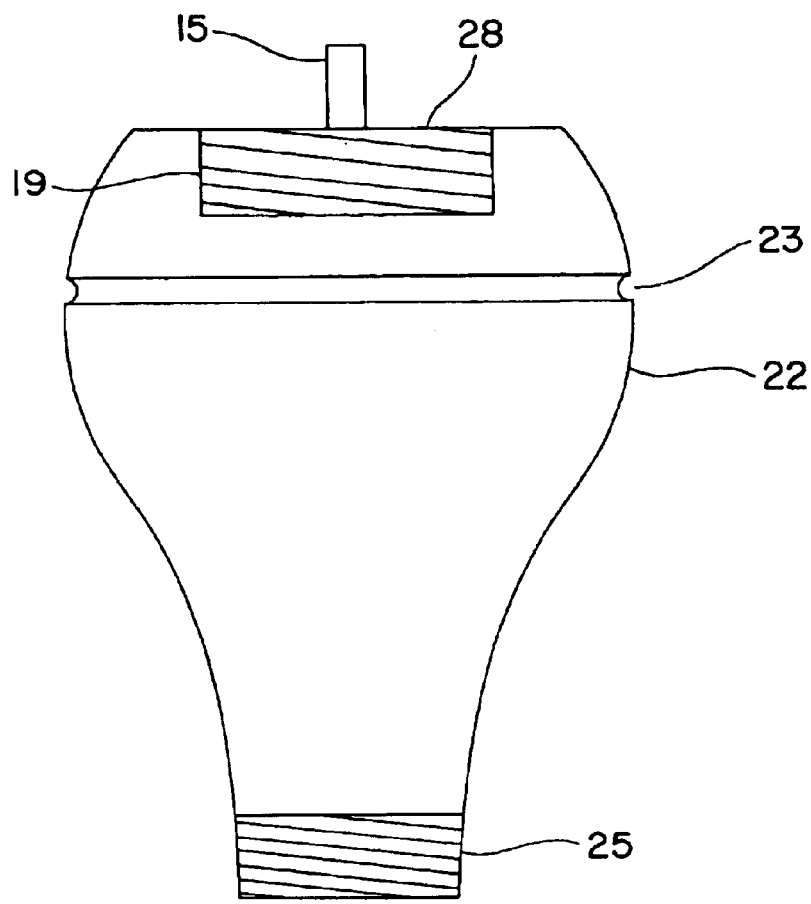
FIG. 1A is a frontal view of the rigid preparation container with a removable vented fill cap and strapping groove.

Referring to FIG. 1A, the ideal quintessence of the reusable vaginal colon and genital cleansing device of the invention consists of a vented fill cap 28, a rigid transparent container 22, a groove 23 that is incorporated around the widest point of rigid transparent container 22 which is used to hold container 22 in an optional storing case. The container 22 is preferably shaped in the likeness of the female uterus with a threaded removable vented fill cap 28 screwed onto the internal threads 19 on the top of container 22. Vented cap 28 has turn tab 15 incorporated onto it to allow the opening and closing of the venting area 16 and has two stop tabs 17 to limit the turning radius of the vent cap and aid in the tightening or loosening of the vented fill cap 28. A volume sensitive valve 27 is installed at the bottom of the retainer 24. The internal threads 18 of the retainer 24 are matched and attach to the external threads 25 on container.

The container 22 is constructed of a durable rigid/flexible transparent plastic such as polyethylene to facilitate the viewing of preparation or fluid level and is formulated with Microban technology. The container 21 must be capable of holding approximately one quart of any of the various preparations.

Figure 1B:
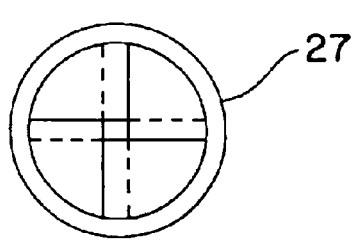
FIG. 1B is a top view of the volume sensitive valve.

Referring to FIG. 1B, depicts a volume sensitive valve 27.

Figure 1C:
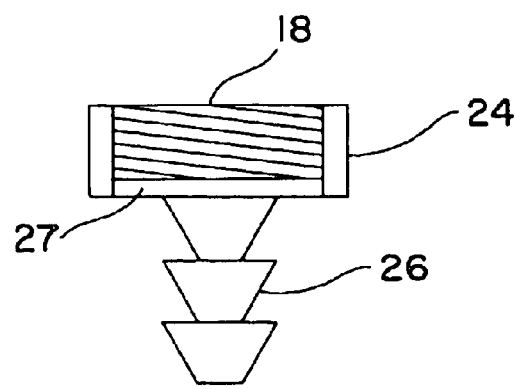
FIG. 1C is a frontal view of the retainer with barbed tube.

Referring to FIG. 1C, depicts retainer 24 with internal thread 8 designed like a heart valve and a barbed tube 26.

Figure 2:
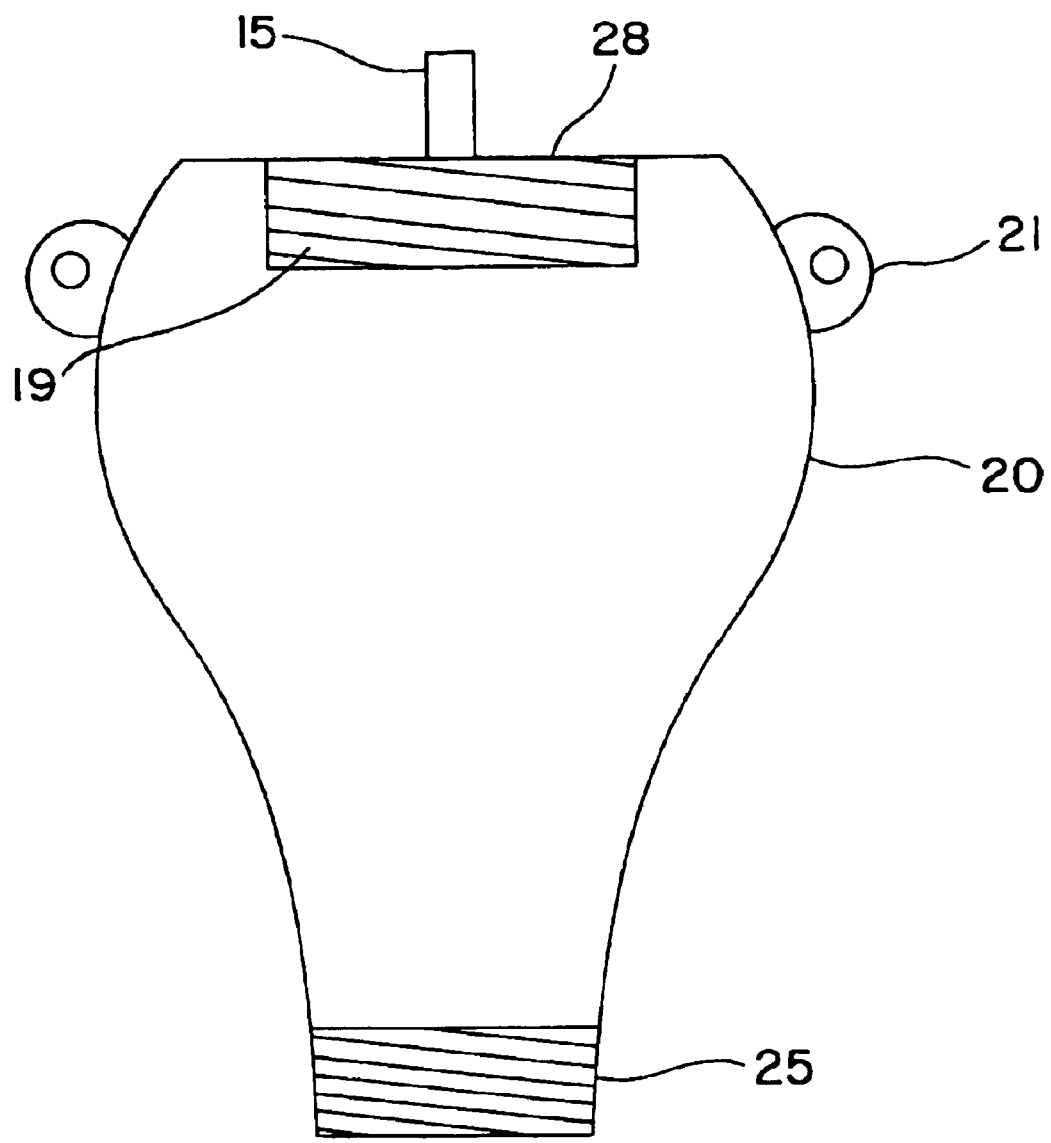
FIG. 2 is a frontal view of the flexible preparation container with hanging eyelets and removable vented fill cap.

Referring to FIG. 2, as shown, incorporates all the attributes of the invention as shown in FIG. 1A, but is constructed with hanging eyelets 2 that are located on both sides of container 20 and of a pliable transparent plastic, which can collapse like an accordion so that it may be carried in a small portable pouch.

Figure 3A:
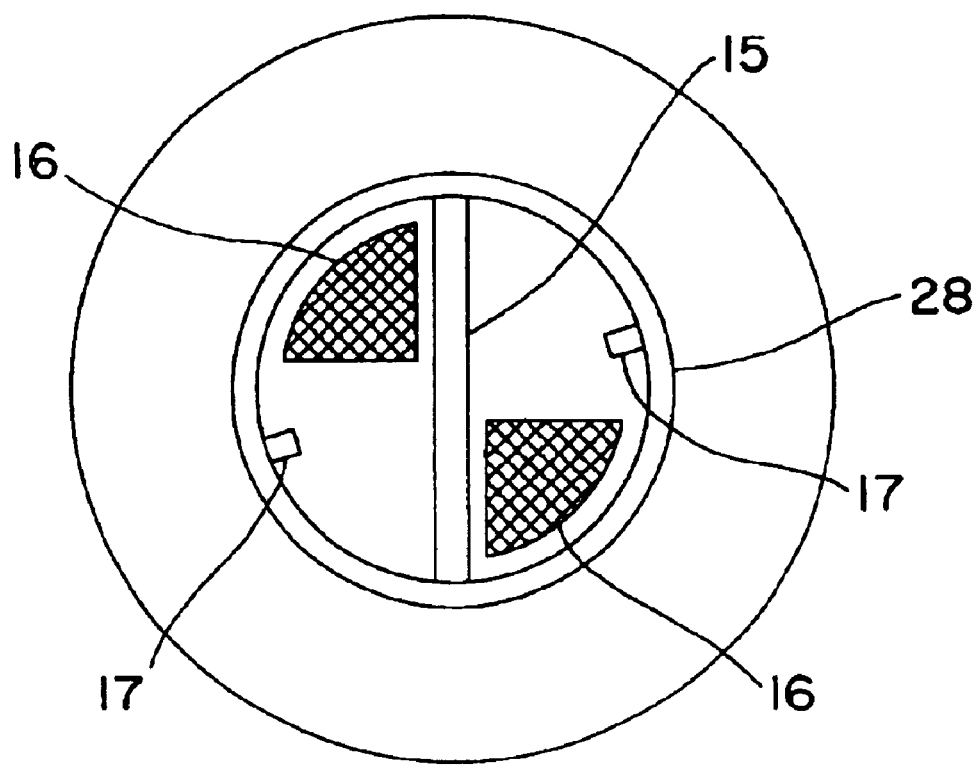
FIG. 3A is a top view of the container and removable vented fill cap.

Referring to FIG. 3A, depicts a top view of the vented fill cap 28 with plastic screen mesh 16 for venting, stop tabs 17 to open or close vent, thumb turn 15 and container 20 or 22.

Figure 3B:
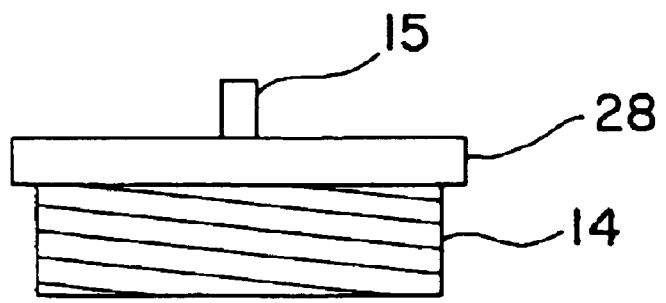
FIG. 3B is a side view of the removable vented fill cap.

Referring to FIG. 3B, depicts a side view of the vented fill cap 28 with threads 14 and thumb turn 15.

Figure 4:
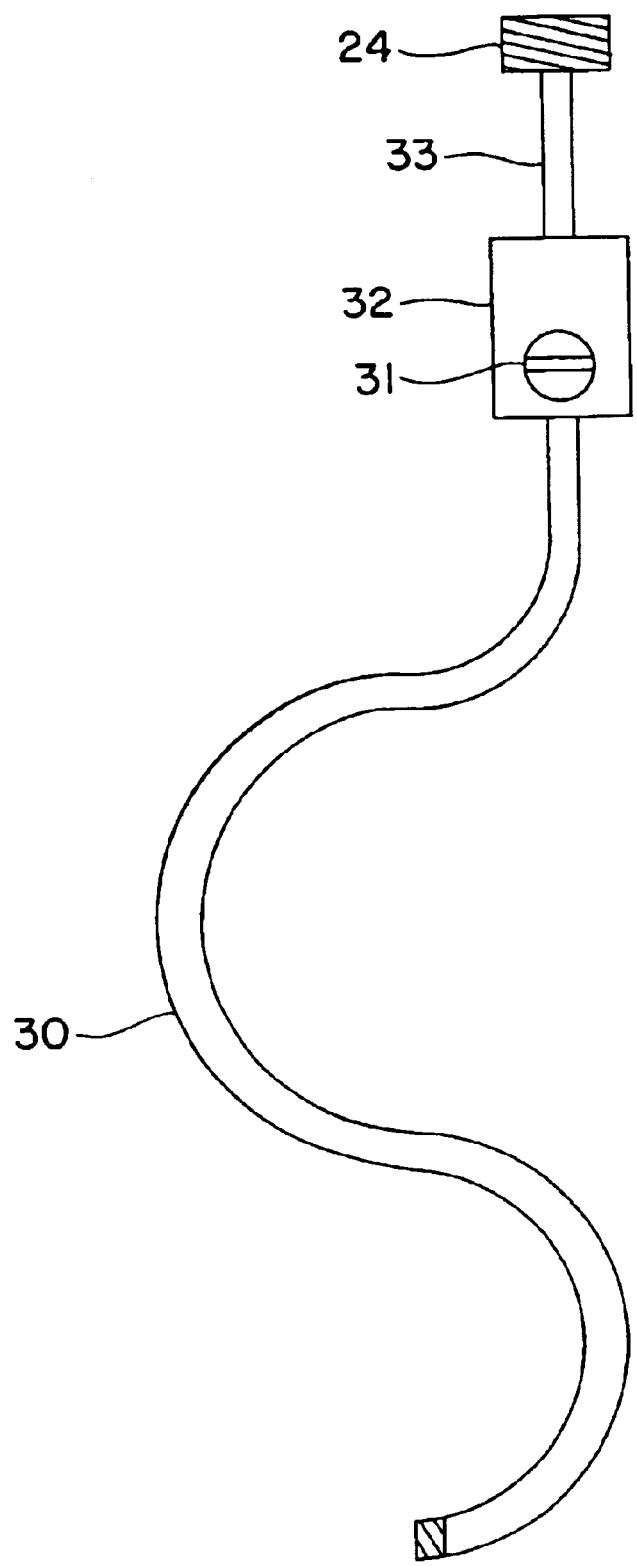
FIG. 4 is a side view of the short flexible tubing, the control valve with ballcheck and an adequate length of hollow tubing.

Referring to FIG. 4, depicts a threaded adaptor 24, a short flexible hollow transparent tube 33 with control valve 32, thumb turn 31, adequate length flexible hollow tubing 30 and thread adaptor 46.

Figure 5A:
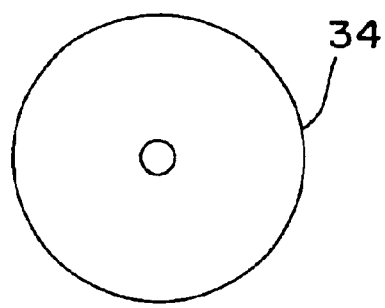
FIG. 5A is a view of the top of the ball check.

Referring to FIG. 5A, depicts the opening 34 at the top portion of the ball check chamber 32.

Figure 5C:
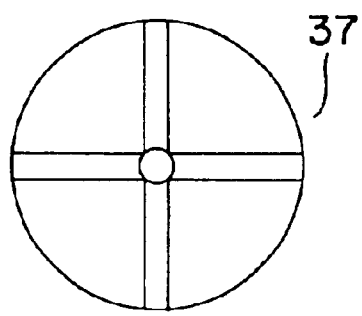
FIG. 5C is a view of the bottom of the ball check.
Figure 5B:
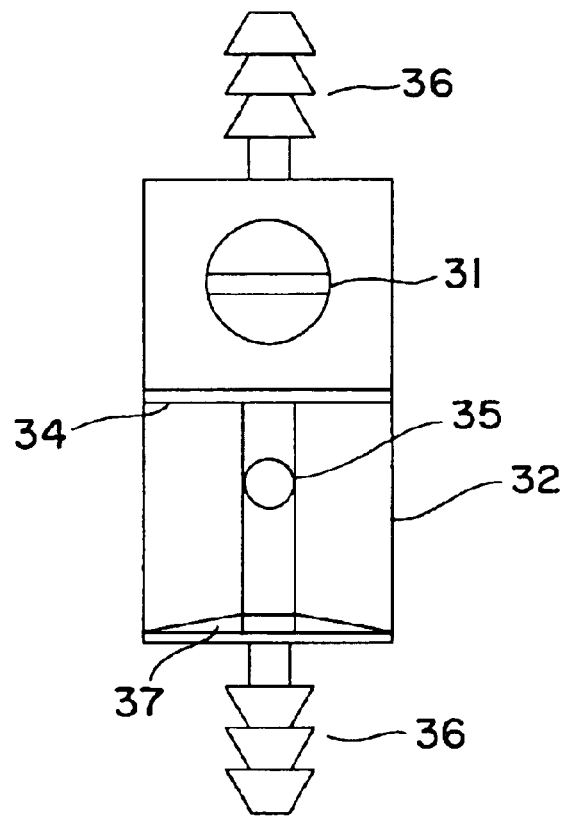
FIG. 5B is a side view of the control valve with ball check and barbed rigid tubes.

Referring to FIG. 5B, depicts the control valve and ball check 32, thumb turn 31 with barbed rigid tubes 36 and ball check 35.

Referring to FIG. 5C, depicts the opening 37 at the bottom portion of the ball check chamber 32.

Figure 6A:
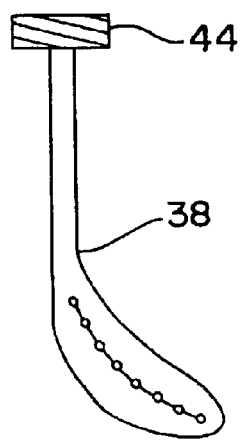
FIG. 6A is a side view of the vaginal cleansing nozzle.

Referring to FIG. 6A, depicts the vaginal nozzle 38 with external threads 44 for attaching onto adaptor on adequate length of flexible tube 30.

Figure 6B:
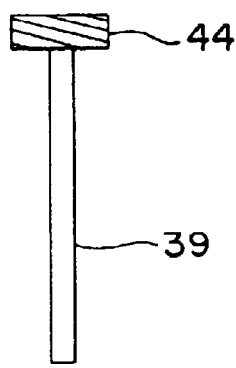
FIG. 6B is a side view of the colon cleansing nozzle.

Referring to FIG. 6B, depicts the enema nozzle 39 with external threads 44 for attaching onto adaptor on adequate length of flexible tube 30.

Figure 6C:
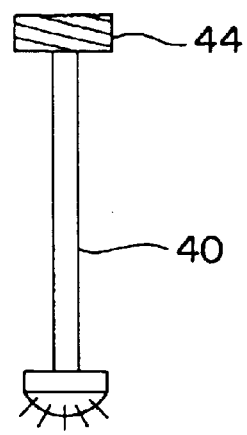
FIG. 6C is a side view of the genital cleansing nozzle.

Referring to FIG. 6C, depicts the genital cleansing nozzle 36 with external threads 35 for attaching onto adaptor of adequate length of flexible hollow tube 30.

Figure 6D:
FIG. 6D is a bottom view of the vaginal cleansing nozzle.

Referring to FIG. 6D, depicts the bottom end of the vaginal cleansing nozzle 41.

Figure 6E:
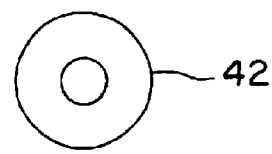
FIG. 6E is a bottom view of the colon cleansing nozzle.

Referring to FIG. 6E, depicts the bottom end of the enema cleansing nozzle 42.

Figure 6F:
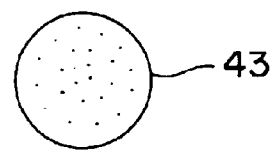
FIG. 6F is a bottom view of the genital cleansing nozzle.

Referring to FIG. 6F, depicts the bottom end of the genital nozzle 43.

Referring to FIG. 6F, depicts the bottom end of the genital nozzle 43.

What is claimed:

1. A hygienic vaginal/colon and genital cleansing device incorporating:
    a container;
    a removable vented fill cap at upper most portion of said container;
    a retainer affixed at its upper end to the lower portion of said container, said retainer having internally threaded opening formed within, extending from the upper to the middle point of said retainer;
    a volume sensitive valve inserted within the formed opening of said retainer; and opens and closes in relation to the liquid or solution weight;
    a short flexible length of hollow tubing secured at one end to the lower end of said retainer and its other end to the top of a control valve;
    a control valve equipped with a ball check with a thumb turn and barbed tubes on either end of length of flexible tubing attached to the top of the control valve,
    the second end of said adequate length of flexible tubing attached to bottom of control valve;
    a nozzle being hollow along its length and curved shaped at attached to bottom of adequate length of tubing;
    a straight rigid nozzle hollow along its length for colon cleansing with one open rounded end and the second end having a fitting with external threads; that are attached to bottom of adequate length of tubing;
    a short rigid tube hollow along its length for external cleansing with a miniature shower head like attachment on one end and with the second end having a fitting with external threads that are attached to adequate length of tubing.

2. The hygienic vaginal/colon and genital cleansing device according to claim 1 wherein the reusable preparation container can be flexible or rigid in construction and able to hold and administer an effective quantity of a cleansing preparation into the vaginal cavity while seated on a toilet.

3. The hygienic vaginal/colon and genital cleansing device according to claim 1 wherein the said reusable preparation container can administer an effective quantity of an enema preparation into the anal cavity while standing in the bathtub with one leg on the rim of a tub.

4. The hygienic vaginal/colon and genital cleansing device according to claim 1 wherein said reusable preparation container can administer an effective quantity of bottled/filtered water onto the genital area for external cleansing while seated on the toilet.

5. The hygienic vaginal/colon and genital cleansing device according to claim 1 wherein the preparation container is formed with likeness to the female uterus, with a removable vented fill cap at its upper most end and with lower most portion of the container capable of accepting a retainer.

6. The hygienic vaginal/colon and genital cleansing device according to claim 1 wherein said retainer is further comprised of a volume sensitive valve to prevent the introduction of air into the vagina or anal cavity, said volume sensitive valve is inserted within the retainer and is constructed as a thin overlapping plastic flexible membrane.

7. The hygienic vaginal/colon and genital cleaning device according to claim 1 said retainer further comprises an extended short rigid barbed tube at its lowest most end capable of accepting a short hollow length of flexible tubing to be connected to it.

8. The hygienic vaginal/colon and genital cleansing device according to claim 1 wherein the second end of short hollow flexible tubing is attached to the top of the control valve, said control valve comprised of a turn valve, a ball check is incorporated within said control valve to prevent backflow of fluids and assembly and adequate length of hollow tubing attached to the bottom of the control valve assembly and a nozzle of choice attached to opposite end of the length of tubing.

9. The hygienic vaginal/colon and genital cleansing device according to claim 8 wherein the lowest portion of said control valve is attached to an adequate length of flexible hollow tubing with an adaptor having external matching threads to attach nozzle of choice.

10. The hygienic vaginal/colon and genital cleansing device according to claim 1 wherein the douching nozzle includes a externally threaded end and a second end that is curved and tip completely closed and is formed with a plurality of four evenly spaced rows of longitudinally disposed holes formed in a series, positioned around the lower two thirds of the length of the nozzle's outer surface which penetrate into the hollow core of said nozzle.

11. The hygienic vaginal/colon and genital cleansing device according to claim 2 wherein the container, and all its components are formed of rigid or flexible plastic formulated with the Microban technology and whereas the effective amount of the douche, enema cleansing preparation, or bottled/filtered water is approximately one quart.

12. The hygienic vaginal/colon and genital cleansing device according to claim 2 wherein the reusable douche, enema or genital cleansing preparation container and all its components are formed of a transparent or translucent plastic such that the level and path of the douche, enema cleansing preparation or bottled/filtered water is visible to the user.

13. The hygienic vaginal/colon and cleansing device according to claim 2 wherein said container flexible or rigid and all its components are constructed of plastic which is combined in formulation with the Microban technology to inhibit the growth of bacteria.

14. The method of douching or colon cleansing utilizing the hygienic vaginal/colon and genital cleansing device according to claim 2 wherein the container is filled depending on application with a pre-measured amount of an over the counter douche, enema mixture which is combined with either bottled/filtered water incorporating, or the use of plain bottled or filtered water;

the connection of flexible hollow tubing with control valve to lower portion of container;

rotating thumb turn on control valve to closed position to prevent premature expulsion of solution;

the removal of the vented fill cap from the container;

pouring an effective amount of filtered/bottled water or preparation into the container;

connecting vented fill cap back onto container;

selecting the nozzle to be used and attaching said nozzle onto adequate length of flexible hollow tubing from control valve;

insertion or placing the nozzle in the orifice or around the area to be cleansed;

gradually opening the control valve;

introducing the preparation which enter and fills the cavity;

with douching while seated on a toilet, insert the vaginal nozzle into the vagina allowing preparation and amassed debris to expelled from the vagina into the toilet aided by the force of gravity, rotating the thumb turn on control valve to open position, allowing the preparation to enter and fill vaginal cavity;

with colon cleansing, while standing in the tub with one leg on the ring of tub, insert the colon cleansing nozzle into the anal cavity, rotating thumb turn allowing enema preparation to enter and fill the anal cavity comfortably, remove colon cleansing nozzle and allow bowel movement to occur;

with genital cleansing, while seated on toilet, place genital cleansing nozzle in front of genitals, rotating thumb turn on control valve to the open position and allowing bottled/filtered water to be sprayed onto the genital area.

15. The method according to claim 13 wherein said steps of opening control valve, allowing contents of said container to flow into respective cavity or onto genital area is repeated until all water or preparation within container is depleted, Process may be repeated if necessary until goals are obtained for colon or genital.

16. The hygienic vaginal/colon and genital cleansing device according to claim 7 wherein the containers and their components are formulated with the Microban compound to prevent pathogen growth for the purpose of cleansing all compounds for future use, the container is filled with a diluted preparation of one quarter of an ounce of chlorhexidine a gentle disinfectant, anti-fungal, anti-microbial and anti-septic compound to one quart of bottled or purified water and allowed to flow through the containers components for the purpose of cleansing all compounds for future use; the container is then filled with plain bottled or purified water and to flush all the components thoroughly; this flushing process is repeated two additional times; the said container and its components are then separated from each other and allowed to dry, then stored for future use.

* * * * *